United States Patent
Tao et al.

(10) Patent No.: US 11,952,604 B2
(45) Date of Patent: *Apr. 9, 2024

(54) ENZYMATIC METHOD FOR PREPARING REBAUDIOSIDE J

(71) Applicant: PepsiCo, Inc., Purchase, NY (US)

(72) Inventors: Alex Tao, Jiangsu (CN); Guoqing Li, Jiangsu (CN); Wenxia Wang, Jiangsu (CN); Leilei Zheng, Jiangsu (CN); Chunlei Zhu, Jiangsu (CN); Xiaoliang Liang, Jiangsu (CN); Kuikiu Chan, Jiangsu (CN)

(73) Assignee: PepsiCo, Inc., Purchase, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/805,626

(22) Filed: Jun. 6, 2022

(65) Prior Publication Data
US 2023/0022453 A1    Jan. 26, 2023

Related U.S. Application Data

(63) Continuation of application No. 16/343,340, filed as application No. PCT/CN2016/102942 on Oct. 21, 2016, now Pat. No. 11,359,222.

(51) Int. Cl.
*C12P 19/56* (2006.01)
*C12N 9/10* (2006.01)

(52) U.S. Cl.
CPC ............ *C12P 19/56* (2013.01); *C12N 9/1051* (2013.01); *C12Y 204/01017* (2013.01)

(58) Field of Classification Search
CPC ............................................ C12Y 204/01017
See application file for complete search history.

(56) References Cited

U.S. PATENT DOCUMENTS

| | | |
|---|---|---|
| 9,243,273 B2 | 1/2016 | Markosyan et al. |
| 9,752,174 B2 | 9/2017 | Markosyan |
| 10,301,662 B2 | 5/2019 | Tao et al. |
| 10,428,364 B2 | 10/2019 | Tao et al. |
| 11,312,985 B2 | 4/2022 | Tao et al. |
| 11,352,653 B2 | 6/2022 | Tao et al. |
| 2010/0099857 A1 | 4/2010 | Evans |
| 2011/0218161 A1 | 9/2011 | Han et al. |
| 2013/0171328 A1 | 7/2013 | Kishore et al. |
| 2014/0271996 A1 | 9/2014 | Prakash et al. |
| 2014/0296499 A1 | 10/2014 | Chen et al. |
| 2014/0357588 A1 | 12/2014 | Markosyan |
| 2015/0315623 A1 | 11/2015 | Mao et al. |
| 2016/0186225 A1 | 6/2016 | Mikkelsen |
| 2016/0298159 A1 | 10/2016 | Tao et al. |
| 2017/0211113 A1 | 7/2017 | Tao et al. |
| 2018/0320211 A1 | 11/2018 | Du et al. |

FOREIGN PATENT DOCUMENTS

| | | |
|---|---|---|
| CA | 2913252 A1 | 12/2014 |
| CN | 103031283 A | 4/2013 |
| CN | 103088041 A | 5/2013 |
| CN | 103179850 A | 6/2013 |
| CN | 103397064 A | 11/2013 |
| CN | 106471128 A | 1/2014 |
| CN | 103757074 A | 4/2014 |
| CN | 103974628 A | 8/2014 |
| CN | 105200098 A | 12/2015 |
| CN | 105492453 A | 4/2016 |
| JP | 2010538621 B1 | 12/2010 |
| JP | 2012504552 A | 2/2012 |
| RU | 2596190 C9 | 10/2016 |
| WO | WO-2010038911 A1 | 4/2010 |
| WO | WO-2011046423 A1 | 4/2011 |
| WO | WO-2011153378 A1 | 12/2011 |
| WO | WO-2012103074 A2 | 8/2012 |
| WO | WO-2013022989 A2 | 2/2013 |
| WO | WO-2013096420 A1 | 6/2013 |
| WO | WO-2013110673 A1 | 8/2013 |
| WO | WO-2013176738 A1 | 11/2013 |
| WO | WO-2014086890 A1 | 6/2014 |
| WO | WO-2014122227 A2 | 8/2014 |
| WO | WO-2014193888 A1 | 12/2014 |
| WO | WO-2014193934 A1 | 12/2014 |
| WO | WO-2015021690 A1 | 2/2015 |
| WO | WO-2015094117 A1 | 6/2015 |
| WO | WO-2015113231 A1 | 8/2015 |
| WO | WO-2016028899 A1 | 2/2016 |
| WO | WO-2016054534 A1 | 4/2016 |
| WO | WO-2016196345 A1 | 12/2016 |

(Continued)

OTHER PUBLICATIONS

Genbank, "UDP-glycosyltransferase 76G 1 [Stevia rebaudiana]," Accession No. AAR06912.1, accessed at http://www.ncbi.nlm.nih.gov/Qrotein/AAR06912, accessed on May 26, 2016, 2 pages.
Genbank, "Os03g0702000 [*Oryza sativa* Japonica Group]," Accession No. NP_001051007.2, accessed at http://www.ncbi.nlm.nih.gov/Qrotein/NP_001051007.2?report=genpept, accessed on May 26, 2016, 4 pages.
Masada, S., et al., "An efficient chemoenzymatic production of small molecule glucosides with in situ UDP-glucose recycling," *FEES Letters* 581 (13):2562-2566, Elsevier B.V., Netherlands (2007).
Ohta, M., et al., "Characterization of Novel Steviol Glycosides from Leaves of Stevia rebaudiana Morita," *J Appl. Glycosci.* 57(3):199-209, The Japanese Society of Applied Glycoscience, Japan (2010).
Wang, Q.J., et al., "*Saccharomyces cerevisiae* surface expression of sucrose synthase," China resources biotechnology and enzyme engineering symposium proceedings (2005).
Wölwer-Rieck, U., "The leaves of Stevia rebaudiana (Bertoni), their constituents and the analyses thereof: a review," *J Agric Food Chem.* 60(4):886-895, American Chemical Society, United States (2012).

(Continued)

*Primary Examiner* — Suzanne M Noakes
(74) *Attorney, Agent, or Firm* — Sterne, Kessler, Goldstein & Fox P.L.L.C.

(57) ABSTRACT

Provided is a method for preparing Rebaudioside J using an enzymatic method, comprising using rebaudioside A as a substrate, and making the substrate, in the presence of a glycosyl donor, react under the catalysis of a UDP-glycosyltransferase-containing recombinant cell and/or UDP-glycosyltransferase prepared therefrom to generate Rebaudioside J.

12 Claims, No Drawings

Specification includes a Sequence Listing.

(56) References Cited

FOREIGN PATENT DOCUMENTS

WO     WO-2017031424 A1     2/2017

OTHER PUBLICATIONS

Pearson, W.R., "An Introduction to Sequence Similarity ("Homology") Searching," *Curr Protoc Bioinformatic*, Author Manuscript, Jun. 3, Wiley, USA (2013).

Whisstock et al. Quarterly Reviews of Biophysics, "Prediction of protein function from protein sequence and structure," 36(3): 307-340 (2003).

Witkowski et al., "Conversion of a beta-ketoacyl synthase to a malonyl decarboxylase by replacement of the active-site cysteine with glutamine," Biochemistry 38(36): 11643-11650 (1999).

Chen, R.R., "Permeability issues in whole-cell bioprocesses and cellular membrane engineering," Appl Microbial Biotechnol 74:730-738 (2007).

UniProtKB—F2DT21 (F2DT21_HORVD), May 31, 2011, accessed at http://www.uniprot.org/uniprot/F2DT21, 4 pages.

Son, M.H. et al., "Production of Flavonoid O-Glucoside Using Sucrose Synthase and Flavonoid O-Glucosyltransferase Fusion Protein," J. Microbiol. Biotechnol. 19(7):709-12, Springer Nature, Switzerland (2009).

Mohamed, A.A et al., "UDP-dependent glycosyltransferases involved in the biosynthesis of steviol glycosides," J Plant Physiol. 168(10): 1136-41, Elsevier, Netherlands (2011).

Branden, C. et al., "Prediction, Engineering, and Design of Protein Structures," Introduction to Protein Structure, Garland Publishing Inc., New York, p. 247 (1991).

Studer, R.A. et al., "Residue mutations and their impact on protein structure and function: detecting beneficial and pathogenic changes," Biochem. J. 44 9: 581-5 94, Biochemical Society, England (2013).

Xu, L. et al., "Progress and strategies on bioethanol production from liganocellulose by consolidated bioprocessing (CBP) using *Saccharyomyces cerevisiae*," Chinese Journal of Biotechnology 26(7): 870-9 (2010).

English Translation of the Written Opinion for International Application No. PCT/CN2016/102948, State Intellectual Property Office of the P.R. China, China, dated Jul. 18, 2017, 3 pages.

English Translation of the International Preliminary Report on Patentability for International Application No. PCT/CN2016/102948, State Intellectual Property Office of the P.R. China, China, dated Apr. 23, 2019, 4 pages.

English Translation of the Written Opinion for International Application No. PCT/CN2016/102910, State Intellectual Property Office of the P.R. China, China, dated Jul. 14, 2017, 3 pages.

English Translation of the International Preliminary Report on Patentability for International Application No. PCT/CN2016/102910, State Intellectual Property Office of the P.R. China, China, dated Apr. 23, 2019, 4 pages.

English Translation of the Written Opinion for International Application No. PCT/CN2016/102942, State Intellectual Property Office of the P.R. China, China, dated Jul. 12, 2017, 4 pages.

English Translation of the International Preliminary Report on Patentability for International Application No. PCT/CN2016/102942, State Intellectual Property Office of the P.R. China, China, dated Apr. 23, 2019, 5 pages.

Supplementary European Search Report for EP Application No. EP 16 91 9469, Berlin, Germany, dated on Jun. 24, 2020, 2 pages.

Supplementary European Search Report for EP Application No. EP 16 91 9379, Berlin, Germany, dated on Jun. 18, 2020, 3 pages.

Wang, J. et al., "[Glycosylation and Glycosyltransferases of Plant Small Molecular Compounds]" *Plant Physiology Communications* 44(5):997-1003, Shandong University, China (2008).

Machine translation of Wang, J. et al. 2008 (cited as document NPL25), Google translate, Jan. 24, 2023, 7 pages.

ENZYMATIC METHOD FOR PREPARING REBAUDIOSIDE J

REFERENCE TO SEQUENCES LISTING SUBMITTED ELECTRONICALLY

The content of the electronically submitted sequence listing, (file name: 3711_9320001_SequenceListing.txt; size: 6,347 bytes; and date of creation: Jun. 6, 2022), filed herewith, is incorporated herein by reference in its entirety.

TECHNICAL FIELD

The present invention relates to a method for preparing Rebaudioside J, and in particular, relates to a biological method for preparing Rebaudioside J.

BACKGROUND

Sweetening agents are a class of food additives that have wide applications in the production of food, beverages, and candies. They may be added in the food production process, or alternatively may be used through appropriate dilution as a substitute for sucrose in household baking. Sweetening agents include natural sweetening agents, for example, sucrose, high fructose corn syrup, honey, etc., and artificial sweetening agents, for example, aspartame, saccharine, etc. Steviosides are a class of natural sweetening agents extracted from the plant *Stevia rebaudiana*, and are widely used in food products and beverages at present. The extract of *Stevia rebaudiana* contains a variety of steviosides comprising rebaudioside. Naturally extracted steviosides have great differences in ingredients across different batches, and need subsequent purification.

The content of Rebaudioside J found in the steviosides of the *Stevia* leaves does not exceed 0.5%; thus, it is extremely difficult to obtain a extract of Rebaudioside J with high purity using the conventional method. Therefore, there are limited the in-depth studies of Rebaudioside J, and the commercial application of Rebaudioside J is hindered.

SUMMARY

The technical problem to be solved by the present invention is to overcome the defects in the prior art. The present invention achieves so by providing a method for preparing Rebaudioside J using an enzymatic method. With such a method, rebaudioside J product with high purity can be produced at a lower cost and with a shorter production cycle.

The following technical solution is employed by the present invention to solve the technical problem described above.

Provided is a method for preparing Rebaudioside J using an enzymatic method, wherein in the method, rebaudioside A is used as a substrate; and in the presence of a glycosyl donor, Rebaudioside J is produced by means of reaction under the catalysis of recombinant cells containing UDP-glycosyltransferase and/or UDP-glycosyltransferase prepared therefrom. UDP-glycosyltransferase (i.e., uridine diphosphoglycosyltransferase), also referred to as UGT, is already well-known.

Preferably, the glycosyl donor is a rhamnosyl donor.

More preferably, the rhamnosyl donor is a UDP-rhamnose.

Preferably, the UDP-glycosyltransferase is a UGT-B from *Oryza sativa* (rice).

Preferably, the amino acid sequence of UGT-B from *Oryza sativa* is at least 60% consistent with Sequence 2 as shown in the Sequence Listing.

More preferably, the amino acid sequence of UGT-B from *Oryza sativa* is at least 70% consistent with Sequence 2 as shown in the Sequence Listing.

Further, the amino acid sequence of UGT-B from *Oryza sativa* is at least 80% consistent with Sequence 2 as shown in the Sequence Listing.

Furthermore, the amino acid sequence of UGT-B from *Oryza sativa* is at least 90% consistent with Sequence 2 as shown in the Sequence Listing.

According to one example, the amino acid sequence of UGT-B from *Oryza sativa* is completely identical with Sequence 2 as shown in the Sequence Listing.

According to the present invention, the reaction is carried out in an aqueous system at a temperature of 4-50° C. and a pH of 5.0 to 9.0. Preferably, the reaction is carried out in an aqueous system at a temperature of 35-45° C. and a pH of 7.5 to 8.5. More Preferably, the reaction is carried out at a temperature of below 40° C. and a pH of below 8.0.

More Preferably, the reaction is carried out in a phosphate buffer solution.

More Preferably, the reaction system contains recombinant cells of UDP-glycosyltransferase and a cell-permeating agent, and the reaction is carried out in the presence of the cell-permeating agent.

Further, the cell-permeating agent is toluene, and the volume ratio concentration of toluene in the reaction system is 1-3%. Furthermore, the volume ratio concentration of toluene is 2%.

More Preferably, all the raw materials used in the reaction are added into a reaction kettle to be uniformly mixed and then placed at a set temperature for reaction while stirring. After the reaction is completed, a Rebaudioside J product which can meet the requirements for use can be obtained through purification-processing. A specific purification method is through post-processing including resin isolation; and a Rebaudioside J product with a purity as high as 95% can be obtained.

Preferably, the recombinant cell is a microbial cell.

More Preferably, the microorganism is *Escherichia coli, Saccharomyces cerevisiae*, or *Pichia pastoris*.

By means of the foregoing technical solution, the present invention has the following advantages in comparison with the prior art:

The method of preparing Rebaudioside J using the enzymatic method provided by the present invention has important application values. As the substrate Rebaudioside A can be obtained in large quantities through using the enzymatic method, the production of Rebaudioside J is no longer limited by the quantity of raw materials. The production cost is thus greatly reduced. It should also be considered that because of the low content of Stevioside in the plant, and there are many Steviosides with different structures, it is rather difficult to extract a product with high purity. When compared with the prior art for extracting Rebaudioside J from *Stevia* leaves, the present invention provides a product with a higher purity by adopting the enzymatic synthesis method, which will promote the research and application of novel Stevioside Rebaudioside J.

DETAILED DESCRIPTION OF THE INVENTION

For the structural formulas of Rebaudioside A and Rebaudioside J, see Formulas I and II respectively.

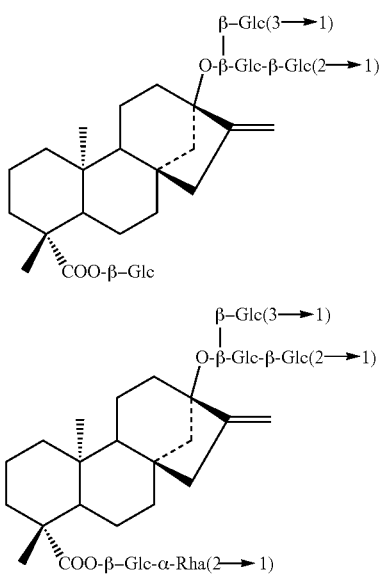

The main synthesis route of Rubadioside J as provided by the present invention is as follows:

The UGT-B adopted in the present invention may exist in the form of lyophilized enzyme powder or in the recombinant cells.

The method for obtaining the UGT-B is as follows:

a recombinant *Escherichia coli* (or the other microorganisms) expression strain of UGT-B is obtained by utilizing molecular cloning technique and genetic engineering technique; then the recombinant *Escherichia coli* is fermented to obtain recombinant cells containing UGT-B, or to prepare and obtain lyophilized powder of UGT-B from the above noted recombinant cells.

Both the molecular cloning technique and the genetic engineering technique described in the present invention are already well-known. The molecular cloning technique may be found in *Molecular Cloning: A Laboratory Manual* (3rd Edition) (J. Sambrook, 2005).

The expression steps of the recombinant strain herein constructed by employing genetic engineering technique are as follows:

(1) (according to Sequence 1 and Sequence 2 as shown in the Sequence Listing) the required gene fragment is genetically synthesized, ligated into a pUC57 vector, while respectively adding NdeI and BamHI enzyme cutting sites at the two ends;

(2) each gene fragment is inserted into the corresponding enzyme cutting site of the expression vector pET30a through double digestion and ligation, so that each gene is placed under the control of T7 promoter; (3) the recombinant plasmid is transformed into *Escherichia coli* BL21 (DE3); the expression of the target protein is induced by utilizing IPTG; and then the expression strains of the recombinant *Escherichia coli* of UGT-B is obtained.

The steps for preparing the recombinant cells containing UGT-B and the lyophilized powder of UGT-B by utilizing the expression strains of the recombinant *Escherichia coli* containing UGT-B are as follows:

the recombinant *Escherichia coli* expression strains containing UGT-B were inoculated into 4 ml of liquid LB medium according to a proportion of 1%; shake cultivation was carried out at 37° C. (at 200 rpm) overnight; the substance cultivated overnight was taken and inoculated into 50 ml of liquid medium according to a proportion of 1%; shake cultivation was carried out at 37° C. (at 200 rpm) overnight until the $OD_{600}$ value reached 0.6-0.8; then IPTG with a final concentration of 0.4 mM was added in at 20° C. for shake cultivation overnight. After the induction is completed, the cells were collected through centrifugation (8,000 rpm, 10 min); then the cells were resuspended with 5 ml 2 mmol/L of phosphate buffer liquid (pH7.0), to obtain the recombinant cells; then the cells were ultrasonically disrupted in ice bath; the homogenate was centrifuged (8,000 rpm, 10 min); and the supernatant was collected and lyophilized for 24 h to obtain the lyophilized powder.

The present invention is further described in details in combination with specific examples.

Example 1: Preparation of the Recombinant *Escherichia Coli* Cells Containing UGT-B According to Sequence 1 and Sequence 2, the UGT-B gene fragment was genetically synthesized, while respectively adding NdeI and BamHI enzyme cutting sites at the two ends, and ligated to the pUC57 vector (produced by Suzhou Jin Wei Zhi Biotech. Co., Ltd.). The UGT gene segment was enzyme cut with restriction endonucleases NdeI and BamHI; and then the segments were recovered and purified; a T4 ligase was added to ligate the segments into the corresponding enzyme cutting sites of pET30a, in order to transform the BL21 (DE3) strains.

The UGT strains were inoculated into 4 ml of liquid LB medium according to a proportion of 1%; shake cultivation was carried out at 37° C. (at 200 rpm) overnight; the substance cultivated overnight was taken and inoculated into 50 ml of liquid LB medium according to a proportion of 1%; shake cultivation was carried out at 37° C. (at 200 rpm) overnight until the $OD_{600}$ value reached 0.6-0.8; then IPTG with a final concentration of 0.4 mM was added in at 20° C. for shake cultivation overnight. After the induction is completed, the cells were collected through centrifugation (8,000 rpm, 10 min); and the collected cells were resuspended with 5 ml 2 mol/L of phosphate buffer (pH 7.0) to obtain the recombinant cells containing UGT-B for catalysis.

Example 2 Preparation of the Lyophilized Powder of UGT-B

The recombinant cells containing UGT-B prepared in Example 1 were ultrasonically disrupted in ice bath; the homogenate was centrifuged (8,000 rpm, 10 min); and the supernatant was collected and lyophilized for 24 h to obtain the lyophilized powder of UGT-B.

Example 3: Synthesis of Rebaudioside J Under the Catalysis of UDP-Glycosyltransferase with Rebaudioside A as the Substrate In this example, lyophilized powder of UGT-B prepared according to the method of Example 2 was used for the catalysis and synthesis of Rebaudioside J.

1 L 0.05 mol/L of phosphate buffer solution (pH8.0), 2 g of UDP Rhamnose, 1 g of Rebaudioside A, 10 g of lyophilized powder of UGT-B were sequentially added into the reaction system, and placed into a water bath at 40° C. after evenly mixing, for reaction for 24 h while stirring at 300 rpm. After the reaction is completed, 500 µl of the reactant solution was added into anhydrous methanol of the equal volume for uniformly mixing; then it was centrifuged at 8,000 rpm for 10 min; and a high performance liquid chromatography was used to detect the supernatant filtration membrane (chromatographic conditions: column: Agilent eclipse sb-C18 4.6×150 mm; detection wavelength: 210 nm; mobile phase: acetonitrile: deionized water=24%: 76%; flow rate: 1.0 mL/min; column temperature: 30° C.). The conversion rate of Rebaudioside A was greater than 90%. After the supernatant was purified by post-processing such as isolating by silica resin and crystallizing, 0.52 g of Rebaudioside J was obtained, and the purity of which was greater than 95%.

Example 4: Synthesis of Rebaudioside J Under the Catalysis of Recombinant Cells of UDP-glycosyltransferase with Rebaudioside A as the Substrate In this example, recombinant cells containing UGT-B prepared according to the method of Example 1 was used for the catalysis and synthesis of Rebaudioside J.

1 L 0.05 mol/L of phosphate buffer solution (pH8.0), 2 g of UDP Rhamnose, 1 g of Rebaudioside A, 20 ml of toluene, 40% of UGT-B whole cells were sequentially added into the reaction system, and placed into a water bath at 40° C. after uniformly mixing, to react for 24 h while stirring at 300 rpm. After the reaction is completed, 500 µl of the reactant solution was taken, and the supernatant was added with anhydrous methanol of the equal volume for uniformly mixing; then it was centrifuged at 8,000 rpm for 10 min; and a high performance liquid chromatography was used to detect the supernatant filtration membrane (chromatographic conditions: column: Agilent eclipse sb-C18 4.6×150 mm; detection wavelength: 210 nm; mobile phase: acetonitrile: deionized water=24%: 76%; flow rate: 1.0 mL/min; column temperature: 30° C.). The conversion rate of Rebaudioside A was greater than 90%. After the supernatant was purified by post-processing such as isolating by silica resin and crystallizing, 0.49 g of Rebaudioside J was obtained, and the purity of which was greater than 95%.

The above-described examples are merely for the illustration of the technical concept and features of the present invention. The object of providing examples is only to allow those skilled in the art to understand the present invention and implement it accordingly; the scope of the present invention is not limited thereto. Any equivalent variations or modifications derived from the essence of the present invention shall fall within the protection scope of the present invention.

The invention claimed is:

1. An enzymatic method for preparing Rebaudioside J, the method comprising reacting Rebaudioside A with a rhamnosyl donor in a reaction system comprising: recombinant cells comprising a UDP-glycosyltransferase, a UDP-glycosyltransferase prepared therefrom, or both the recombinant cells comprising the UDP-glycosyltransferase and the UDP-glycosyltransferase prepared therefrom, wherein the UDP-glycosyltransferase comprises an amino acid sequence having at least 80% sequence identity to SEQ ID NO: 2, wherein Rebaudioside A is converted to Rebaudioside J at a conversion rate greater than 90%.

2. The method of claim 1, wherein the UDP-glycosyltransferase comprises an amino acid sequence having at least 90% sequence identity to SEQ ID NO: 2.

3. The method of claim 2, wherein the rhamnosyl donor is a UDP-rhamnose.

4. The method of claim 2, wherein the UDP-glycosyltransferase is a UGT-B from *Oryza sativa*.

5. The method of claim 2, wherein the reaction system is aqueous and has a temperature of 35-45° C. and a pH of 7.5 to 8.5.

6. The method of claim 5, wherein the reaction system comprises a phosphate buffer solution.

7. The method of claim 5, wherein the reaction system further comprises a cell-permeabilizing agent.

8. The method of claim 7, wherein the cell-permeabilizing agent is toluene and wherein the toluene has a concentration by volume of 1-3%.

9. The method of claim 2, wherein the recombinant cell is a cell of a microorganism.

10. The method of claim 9, wherein the microorganism is *Escherichia coli, Saccharomyces cerevisiae*, or *Pichia pastoris*.

11. The method of claim 2, further comprising purifying the Rebaudioside J via resin isolation.

12. The method of claim 11, wherein the Rebaudioside J purified via resin isolation has a purity greater than 95%.

* * * * *

SEQUENCE LISTING

```
<160> NUMBER OF SEQ ID NOS: 2

<210> SEQ ID NO 1
<211> LENGTH: 1389
<212> TYPE: DNA
<213> ORGANISM: Artificial Sequence
<220> FEATURE:
<223> OTHER INFORMATION: Synthesized nucleotide sequence

<400> SEQUENCE: 1
atggacagcg gttactcttc tagctatgct gcggcagccg gtatgcacgt agttatttgt      60
ccgtggctcg ctttcggtca cctcctgccg tgcctggacc tggcgcagcg cctggcatct     120
cgtggtcacc gtgtcagttt cgttagcacg ccgcgtaaca tctcacgtct gccgccggtc     180
cgtccggctc tggccccgct ggttgcgttc gttgcgctac ctctgccgcg cgttgaaggc     240
ttaccggatg gcgcagagtc taccaacgac gtgccgcacg atcgcccgga tatggttgaa     300
ctccaccgcc gtgcatttga cggtctggca gctccgttct ccgaatttct gggtaccgcg     360
tgtgccgact gggtcatcgt agacgtattc caccactggg cagctgcagc ggctttagaa     420
cacaaagtac cgtgcgcaat gatgctgctg ggctctgctc acatgatcgc gtctattgcc     480
gaccgtcgtc tggaacgtgc agagaccgaa tctccagcgg cagccggtca gggccgtcct     540
gcagctgctc cgaccttcga agttgctcgt atgaagctca tccgcactaa aggttcttcc     600
ggtatgtcac tggcagagcg tttctcgctg acgctctccc gtagcagcct ggttgtgggg     660
cgctcctgcg tggaattcga accggaaact gtgccgctac tgtctaccct gcgtggcaag     720
```

-continued

```
ccgatcactt ttctgggtct catgccgcca ctgcacgaag gtcgccgcga agacggtgaa      780
gatgctacgg ttcgttggtt ggacgcccag ccggctaaaa gcgtcgtgta cgtagctctg      840
ggcagtgaag ttccattggg tgtcgagaaa gtgcatgaac tggctttggg tctggagctg      900
gctggcaccc gttcctctg gcactgcgt aagccgactg gtgtgtctga tgctgacctt       960
ctgccggctg gtttcgaaga acgtacccgt ggtcgcggcg tagtggcaac ccgctgggta     1020
ccgcagatgt ccatcctggc acacgctgct gttggcgcgt tcttaccca ctgcgggtgg      1080 aactctacaa tcgaaggcct gatgttcggc catcctctga ttatgctgcc aatcttcggt    1140
gatcagggtc cgaacgctcg tctgatcgaa gccaaaaacg ccggcttaca gtcgcacgc     1200 aacgacggcg atggttcttt cgatcgtgaa ggtgttgcgg cagctatccg tgcagtggct    1260
gtagaagaag agtcgagcaa agtgttccag gcaaaagcca aaaagctgca ggaaatcgtt   1320
gcggacatgg cgtgccacga acgttacatc gatggcttta tccagcagct gcgctcctac    1380
aaagattaa                                                            1389
```

<210> SEQ ID NO 2
<211> LENGTH: 462
<212> TYPE: PRT
<213> ORGANISM: Artificial Sequence
<220> FEATURE:
<223> OTHER INFORMATION: Synthesized protein sequence

<400> SEQUENCE: 2

```
Met Asp Ser Gly Tyr Ser Ser Tyr Ala Ala Ala Ala Gly Met His
1               5                   10                  15

Val Val Ile Cys Pro Trp Leu Ala Phe Gly His Leu Leu Pro Cys Leu
                20                  25                  30

Asp Leu Ala Gln Arg Leu Ala Ser Arg Gly His Arg Val Ser Phe Val
            35                  40                  45

Ser Thr Pro Arg Asn Ile Ser Arg Leu Pro Pro Val Arg Pro Ala Leu
        50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Ala Gly
                165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
        195                 200                 205

Ser Leu Thr Leu Ser Arg Ser Ser Leu Val Val Gly Arg Ser Cys Val
    210                 215                 220

Glu Phe Glu Pro Glu Thr Val Pro Leu Leu Ser Thr Leu Arg Gly Lys
225                 230                 235                 240
```

-continued

```
Pro Ile Thr Phe Leu Gly Leu Met Pro Pro Leu His Glu Gly Arg Arg
            245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val
            275                 280                 285

Glu Lys Val His Glu Leu Ala Leu Gly Leu Glu Leu Ala Gly Thr Arg
            290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
            325                 330                 335

Thr Arg Trp Val Pro Gln Met Ser Ile Leu Ala His Ala Ala Val Gly
            340                 345                 350

Ala Phe Leu Thr His Cys Gly Trp Asn Ser Thr Ile Glu Gly Leu Met
            355                 360                 365

Phe Gly His Pro Leu Ile Met Leu Pro Ile Phe Gly Asp Gln Gly Pro
            370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
            405                 410                 415

Arg Ala Val Ala Val Glu Glu Glu Ser Ser Lys Val Phe Gln Ala Lys
            420                 425                 430

Ala Lys Lys Leu Gln Glu Ile Val Ala Asp Met Ala Cys His Glu Arg
            435                 440                 445

Tyr Ile Asp Gly Phe Ile Gln Gln Leu Arg Ser Tyr Lys Asp
450                 455                 460
```